(12) United States Patent
Rafiee et al.

(10) Patent No.: US 11,871,928 B2
(45) Date of Patent: *Jan. 16, 2024

(54) DEVICES AND METHODS FOR EFFECTUATING PERCUTANEOUS SHUNT PROCEDURES

(71) Applicant: Transmural Systems LLC, Andover, MA (US)

(72) Inventors: Nasser Rafiee, Andover, MA (US); Stuart MacDonald, Andover, MA (US); Biwei MacDonald, Andover, MA (US); Alana Rafiee, Andover, MA (US)

(73) Assignee: Transmural Systems LLC, Andover, MA (US)

( * ) Notice: Subject to any disclaimer, the term of this patent is extended or adjusted under 35 U.S.C. 154(b) by 272 days.

This patent is subject to a terminal disclaimer.

(21) Appl. No.: 17/462,190

(22) Filed: Aug. 31, 2021

(65) Prior Publication Data

US 2022/0125430 A1 Apr. 28, 2022

Related U.S. Application Data

(63) Continuation of application No. 16/399,670, filed on Apr. 30, 2019, now Pat. No. 11,179,156, which is a
(Continued)

(51) Int. Cl.
*A61F 2/06* (2013.01)
*A61B 17/11* (2006.01)
(Continued)

(52) U.S. Cl.
CPC .............. *A61B 17/11* (2013.01); *A61F 2/064* (2013.01); *A61M 25/00* (2013.01);
(Continued)

(58) Field of Classification Search
CPC ...... A61F 2/06; A61F 2/07; A61F 2/95; A61F 2/966; A61F 2/064; A61B 17/11; A61M 25/00

See application file for complete search history.

(56) References Cited

U.S. PATENT DOCUMENTS

| 4,106,129 A | 8/1978 | Carpentier et al. |
| 4,259,753 A | 4/1981 | Liotta et al. |

(Continued)

FOREIGN PATENT DOCUMENTS

| EP | 2412397 A1 | 2/2012 |
| JP | 2015519969 A | 7/2015 |

(Continued)

OTHER PUBLICATIONS

International Search Report dated Jun. 16, 2022 in International Patent Application No. PCT/US2022/018806.

(Continued)

*Primary Examiner* — Vi X Nguyen
(74) *Attorney, Agent, or Firm* — Dewitt, LLP; Brian R. Pollack, Esq.

(57) ABSTRACT

In some implementations, a radially self-expanding endograft prosthesis is provided that includes (i) distal flange that is self-expanding and configured to flip generally perpendicularly with respect to a body of the prosthesis to help seat the prosthesis against a tissue wall, (ii) a distal segment extending proximally from the distal flange that has sufficient stiffness to maintain a puncture open that is formed through a vessel wall (iii) a compliant middle segment extending proximally from the distal segment, the middle segment being more compliant than the distal segment, and having independently movable undulating strut rings attached to a tubular fabric, the combined structure providing flexibility and compliance to allow for full patency while flexed, the segment being configured to accommodate up to (Continued)

a 90 degree bend, (iv) a proximal segment having a plurality of adjacent undulating strut rings that are connected to each other.

18 Claims, 13 Drawing Sheets

Related U.S. Application Data continuation of application No. 15/267,075, filed on Sep. 15, 2016, now Pat. No. 10,426,482.

(60) Provisional application No. 62/363,716, filed on Jul. 18, 2016, provisional application No. 62/219,118, filed on Sep. 15, 2015.

(51) Int. Cl.
*A61M 25/00* (2006.01)
*A61B 17/00* (2006.01)
*A61F 2/07* (2013.01)
*A61F 2/82* (2013.01)
*A61F 2/915* (2013.01)

(52) U.S. Cl.
CPC ............... *A61B 2017/00252* (2013.01); *A61B 2017/1107* (2013.01); *A61B 2017/1139* (2013.01); *A61F 2/07* (2013.01); *A61F 2002/828* (2013.01); *A61F 2002/91575* (2013.01); *A61F 2250/0029* (2013.01); *A61F 2250/0039* (2013.01); *A61F 2250/0082* (2013.01); *A61F 2250/0098* (2013.01)

(56) References Cited

U.S. PATENT DOCUMENTS

| | | |
|---|---|---|
| 4,666,442 A | 5/1987 | Arru et al. |
| 4,692,164 A | 9/1987 | Dzemeshkevich et al. |
| 5,411,552 A | 5/1995 | Andersen et al. |
| 5,449,384 A | 9/1995 | Johnson |
| 5,606,928 A | 3/1997 | Religa et al. |
| 5,639,278 A | 6/1997 | Dereume et al. |
| 5,749,921 A | 5/1998 | Lenker et al. |
| 5,788,715 A | 8/1998 | Watson, Jr. et al. |
| 5,861,028 A | 1/1999 | Angell |
| 5,895,410 A | 4/1999 | Forber et al. |
| 5,928,281 A | 7/1999 | Huynh et al. |
| 6,059,769 A | 5/2000 | Lunn et al. |
| 6,090,136 A * | 7/2000 | McDonald ............ A61F 2/92 623/1.23 |
| 6,106,510 A | 8/2000 | Lunn et al. |
| 6,238,430 B1 | 5/2001 | Klumb et al. |
| 6,375,774 B1 | 4/2002 | Lunn et al. |
| 6,599,303 B1 | 7/2003 | Peterson |
| 6,602,271 B2 | 8/2003 | Adams et al. |
| 6,716,231 B1 | 4/2004 | Rafiee et al. |
| 6,733,525 B2 | 5/2004 | Yang et al. |
| 6,790,229 B1 | 9/2004 | Berreklouw |
| 6,797,000 B2 | 9/2004 | Simpson et al. |
| 6,800,081 B2 | 10/2004 | Parodi |
| 6,866,677 B2 | 3/2005 | Douk et al. |
| 6,911,036 B2 | 6/2005 | Douk et al. |
| 6,926,690 B2 | 8/2005 | Renati |
| 6,953,476 B1 | 10/2005 | Shalev |
| 6,960,217 B2 | 11/2005 | Bolduc |
| 7,044,958 B2 | 5/2006 | Douk et al. |
| 7,066,946 B2 | 6/2006 | Douk et al. |
| 7,137,993 B2 | 11/2006 | Acosta |
| 7,189,259 B2 | 3/2007 | Simionescu et al. |
| 7,195,641 B2 | 3/2007 | Palmaz et al. |
| 7,201,772 B2 | 4/2007 | Schwammenthal et al. |
| 7,294,135 B2 | 11/2007 | Stephens et al. |
| 7,316,706 B2 | 1/2008 | Bloom et al. |
| 7,399,315 B2 | 7/2008 | Iobbi |
| 7,425,219 B2 | 9/2008 | Quadri |
| 7,442,204 B2 | 10/2008 | Schwammenthal et al. |
| 7,442,207 B2 | 10/2008 | Rafiee |
| 7,445,631 B2 | 11/2008 | Salahieh et al. |
| 7,481,838 B2 | 1/2009 | Carpentier et al. |
| 7,491,232 B2 | 2/2009 | Bolduc et al. |
| 7,524,330 B2 | 4/2009 | Berreklouw |
| 7,655,040 B2 | 2/2010 | Douk et al. |
| 7,682,352 B2 | 3/2010 | Rafiee et al. |
| 7,699,892 B2 | 4/2010 | Rafiee et al. |
| 7,716,801 B2 | 5/2010 | Douk et al. |
| 7,753,840 B2 | 7/2010 | Simionescu et al. |
| 7,753,949 B2 | 7/2010 | Lamphere et al. |
| 7,780,726 B2 | 8/2010 | Seguin |
| 7,799,069 B2 | 9/2010 | Bailey et al. |
| 7,806,917 B2 | 10/2010 | Xiao |
| 7,806,919 B2 | 10/2010 | Bloom et al. |
| 7,815,673 B2 | 10/2010 | Bloom et al. |
| 7,947,072 B2 | 5/2011 | Yang et al. |
| 7,955,384 B2 | 6/2011 | Rafiee et al. |
| 7,972,370 B2 | 7/2011 | Douk et al. |
| 7,998,188 B2 | 8/2011 | Zilla et al. |
| 8,002,825 B2 | 8/2011 | Letac et al. |
| 8,052,750 B2 | 11/2011 | Tuval et al. |
| 8,062,355 B2 | 11/2011 | Figulla et al. |
| 8,070,802 B2 | 12/2011 | Lamphere et al. |
| 8,092,518 B2 | 1/2012 | Schreck |
| 8,092,520 B2 | 1/2012 | Quadri |
| 8,092,524 B2 | 1/2012 | Nugent et al. |
| 8,226,710 B2 | 7/2012 | Nguyen et al. |
| 8,252,051 B2 | 8/2012 | Chau et al. |
| 8,308,798 B2 | 11/2012 | Pintor et al. |
| 8,337,541 B2 | 12/2012 | Quadri et al. |
| 8,348,995 B2 | 1/2013 | Tuval et al. |
| 8,348,996 B2 | 1/2013 | Tuval et al. |
| 8,353,954 B2 | 1/2013 | Cai et al. |
| 8,353,955 B2 | 1/2013 | Styrc et al. |
| 8,518,096 B2 | 8/2013 | Nelson |
| 10,426,482 B2 | 10/2019 | Rafiee et al. |
| 11,179,156 B2 * | 11/2021 | Rafiee .................. A61M 25/00 |
| 2001/0021872 A1 | 9/2001 | Bailey et al. |
| 2002/0032481 A1 | 3/2002 | Gabbay |
| 2002/0138138 A1 | 9/2002 | Yang |
| 2003/0055495 A1 | 3/2003 | Pease et al. |
| 2003/0065386 A1 | 4/2003 | Weadock |
| 2003/0097172 A1 | 5/2003 | Shalev et al. |
| 2004/0087998 A1 | 5/2004 | Lee et al. |
| 2004/0127916 A1 | 7/2004 | Bolduc et al. |
| 2005/0038508 A1 | 2/2005 | Gabbay |
| 2005/0043790 A1 | 2/2005 | Seguin |
| 2005/0049675 A1 | 3/2005 | Wallace |
| 2005/0055082 A1 | 3/2005 | Ben-Muvhar et al. |
| 2005/0137769 A1 | 6/2005 | Salahieh et al. |
| 2005/0143809 A1 | 6/2005 | Salahieh et al. |
| 2005/0177180 A1 | 8/2005 | Kaganov et al. |
| 2005/0288706 A1 | 12/2005 | Widomski et al. |
| 2006/0085012 A1 | 4/2006 | Dolan |
| 2006/0106449 A1 | 5/2006 | Ben-Muvhar |
| 2006/0106450 A1 | 5/2006 | Ben-Muvhar |
| 2006/0173537 A1 | 8/2006 | Yang et al. |
| 2007/0043435 A1 | 2/2007 | Seguin et al. |
| 2007/0067029 A1 | 3/2007 | Gabbay |
| 2007/0250160 A1 | 10/2007 | Rafiee |
| 2007/0255398 A1 | 11/2007 | Yang et al. |
| 2007/0288089 A1 | 12/2007 | Gurskis et al. |
| 2007/0293942 A1 | 12/2007 | Mizraee |
| 2008/0015687 A1 | 1/2008 | Lashinski et al. |
| 2008/0021537 A1 | 1/2008 | Ben-Muvhar et al. |
| 2008/0065191 A1 | 3/2008 | Bolduc et al. |
| 2008/0077234 A1 | 3/2008 | Styrc |
| 2008/0125860 A1 | 5/2008 | Webler et al. |
| 2008/0208328 A1 | 8/2008 | Antocci et al. |
| 2008/0221672 A1 | 9/2008 | Lamphere et al. |
| 2009/0005863 A1 | 1/2009 | Goetz et al. |
| 2009/0062841 A1 | 3/2009 | Amplatz et al. |
| 2009/0270966 A1 | 10/2009 | Douk et al. |
| 2009/0270976 A1 | 10/2009 | Douk et al. |
| 2009/0306768 A1 | 12/2009 | Quadri |

(56) References Cited

U.S. PATENT DOCUMENTS

| | | |
|---|---|---|
| 2009/0319038 A1 | 12/2009 | Gurskis et al. |
| 2010/0036479 A1 | 2/2010 | Hill et al. |
| 2010/0082094 A1 | 4/2010 | Quadri et al. |
| 2010/0100167 A1 | 4/2010 | Bortlein et al. |
| 2010/0174363 A1 | 7/2010 | Castro |
| 2010/0179648 A1 | 7/2010 | Richter et al. |
| 2010/0179649 A1 | 7/2010 | Richter et al. |
| 2010/0185275 A1 | 7/2010 | Richter et al. |
| 2010/0249923 A1 | 9/2010 | Alkhatib et al. |
| 2010/0262232 A1 | 10/2010 | Annest |
| 2010/0280606 A1 | 11/2010 | Naor |
| 2010/0298931 A1 | 11/2010 | Quadri et al. |
| 2011/0112632 A1 | 5/2011 | Chau et al. |
| 2011/0137409 A1 | 6/2011 | Yang et al. |
| 2011/0172784 A1 | 7/2011 | Richter et al. |
| 2011/0282438 A1 | 11/2011 | Drews et al. |
| 2011/0313515 A1 | 12/2011 | Quadri et al. |
| 2011/0319988 A1 | 12/2011 | Schankereli et al. |
| 2011/0319989 A1 | 12/2011 | Lane et al. |
| 2012/0022639 A1 | 1/2012 | Hacohen |
| 2012/0059450 A1 | 3/2012 | Chiang et al. |
| 2012/0065652 A1 | 3/2012 | Cully et al. |
| 2012/0078353 A1 | 3/2012 | Quadri et al. |
| 2012/0078360 A1 | 3/2012 | Rafiee |
| 2012/0143141 A1* | 6/2012 | Verkaik ............... A61M 60/178 604/174 |
| 2012/0179244 A1 | 7/2012 | Schankereli et al. |
| 2012/0215303 A1 | 8/2012 | Quadri et al. |
| 2012/0316642 A1 | 12/2012 | Yu et al. |
| 2012/0323316 A1 | 12/2012 | Chau et al. |
| 2014/0018906 A1 | 1/2014 | Rafiee |
| 2014/0128965 A1 | 5/2014 | Rafiee |
| 2014/0163668 A1 | 6/2014 | Rafiee |
| 2014/0358223 A1 | 12/2014 | Rafiee et al. |
| 2014/0039083 A1 | 2/2015 | Rafiee |
| 2015/0134051 A1 | 5/2015 | Donadio et al. |
| 2019/0231510 A1 | 8/2019 | Rafiee et al. |

FOREIGN PATENT DOCUMENTS

| | | |
|---|---|---|
| KR | 20130110413 A1 | 10/2013 |
| KR | 101501614 B1 | 3/2015 |
| RU | 100 718 U1 | 12/2010 |
| WO | WO2007121314 A2 | 10/2007 |
| WO | WO2012061809 A2 | 5/2012 |
| WO | WO2013131069 A1 | 9/2013 |
| WO | WO2015069947 A1 | 5/2015 |
| WO | WO2015148821 A1 | 10/2015 |

OTHER PUBLICATIONS

Written Opinion of the International Searching Authority dated May 17, 2022 in International Patent Application No. PCT/US2022/018806.

International Search Report, for related application No. PCT/US2011/059586, dated May 25, 2012.

International Preliminary Report on Patentability and Written Opinion, or related application No. PCT/US2011/059586, dated May 25, 2012.

BioIntegral Surgical, Mitral Valve Restoration System.

International Search Report for co-pending international application No. PCT/US2013/028774, dated Jun. 14, 2013.

International Preliminary Report on Patentability and Written Opinion, on related application No. PCT/US2014/064431 dated Mar. 26, 2015.

International Search Report, for related application No. PCT/US2015/022782, dated Jun. 18, 2015.

International Search Report and Written Opinion in Application No. PCT/US2016/052005, dated Dec. 29, 2016.

International Search Report and Written Opinion in Application No. PCT/US2018/049373, dated Dec. 6, 2018.

Office Action in related Japanese Patent Application No. JP2018-514884 dated Jun. 30, 2020 with English language translation.

\* cited by examiner

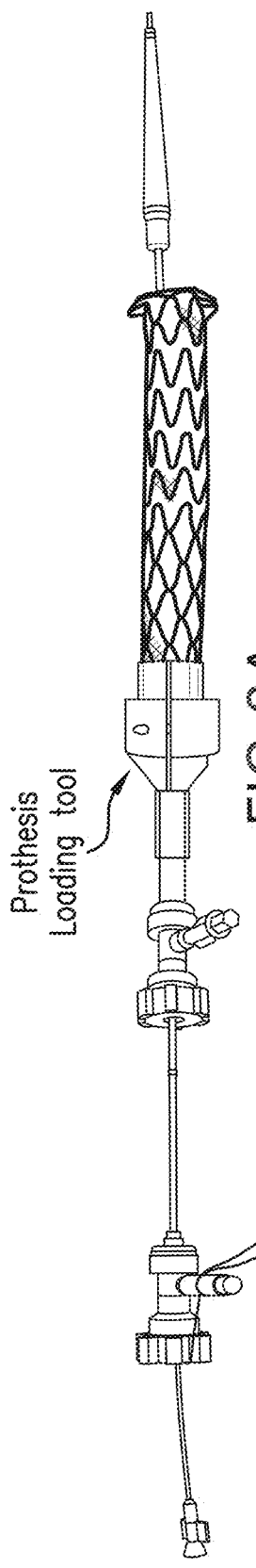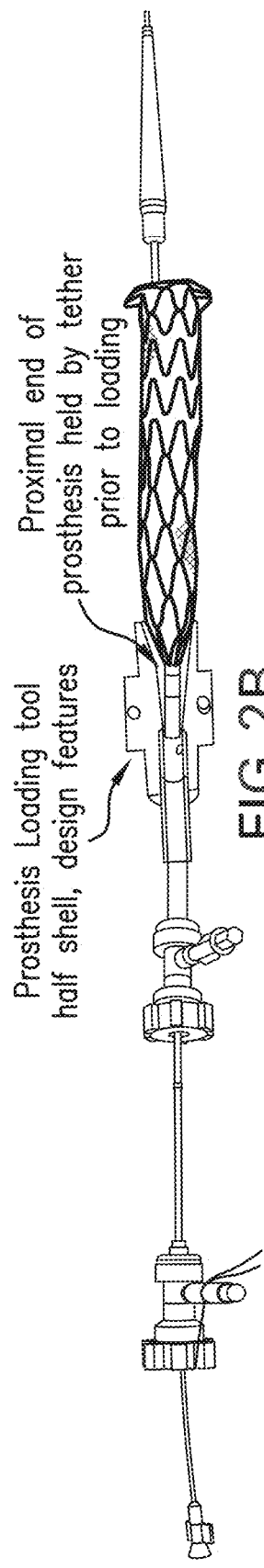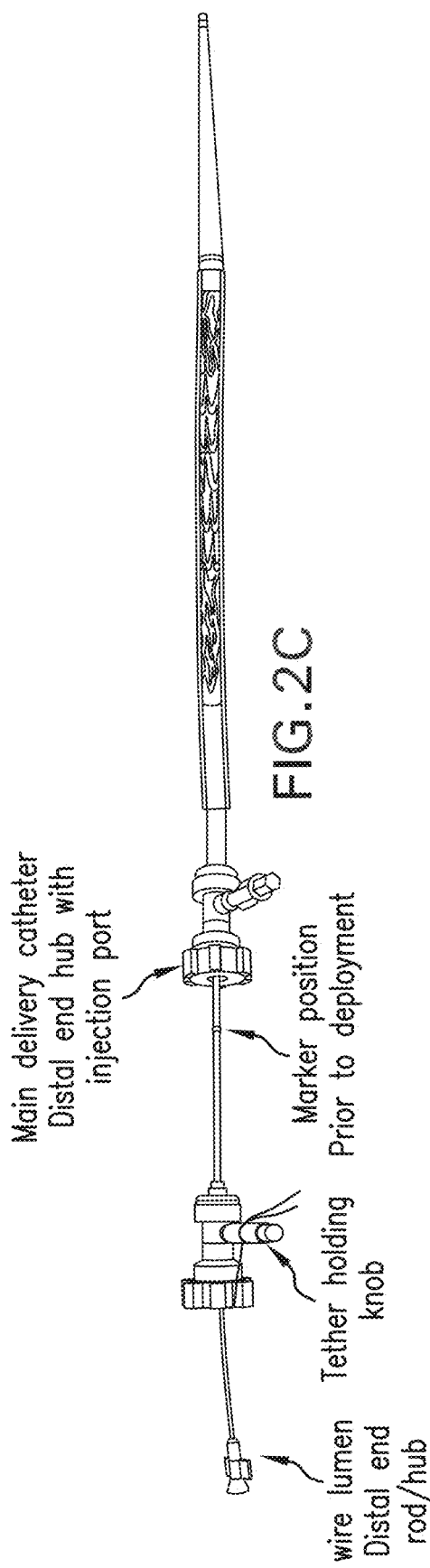

Fenestration 2 openings, opposite sides

Both Glenn and Fontan deployed Percutaneously in one animal under Bi-plane X-Ray and MRI The Glenn Shunt supply blood from the Superior Vena Cava (SVC) to Main Pulmonary Artery (MPA)

The Fontan supply blood from the Inferior Vena Cava (IVC) to Main Pulmonary Artery (MPA)

FIG. 7

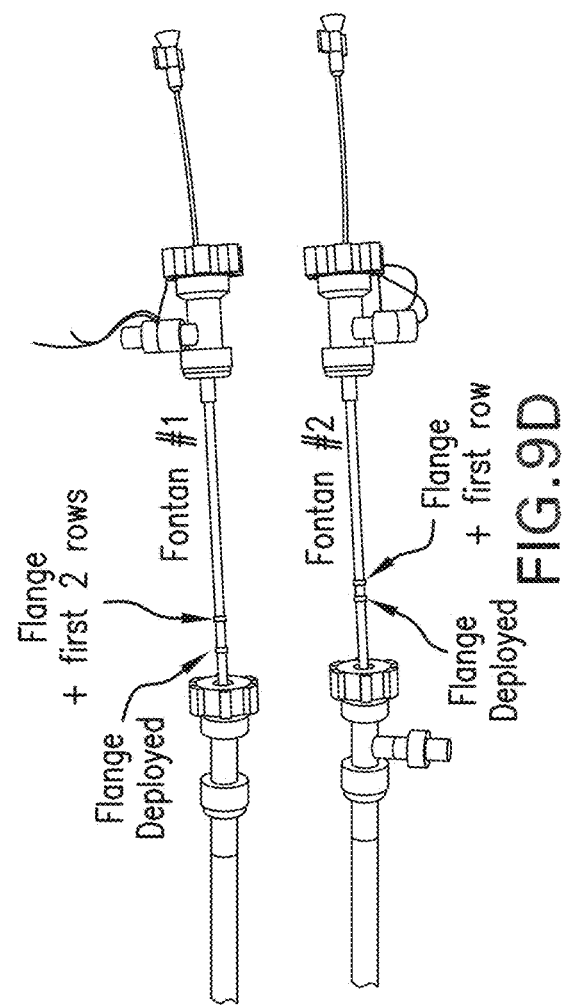
FIG. 9D
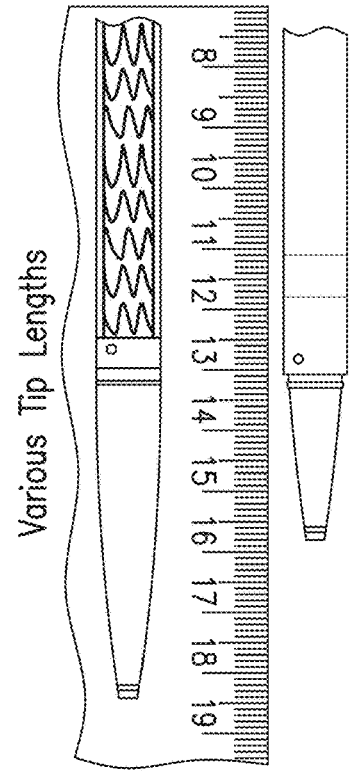
FIG. 9E
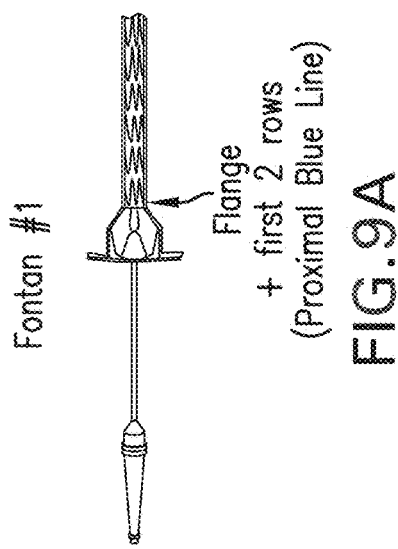
FIG. 9A
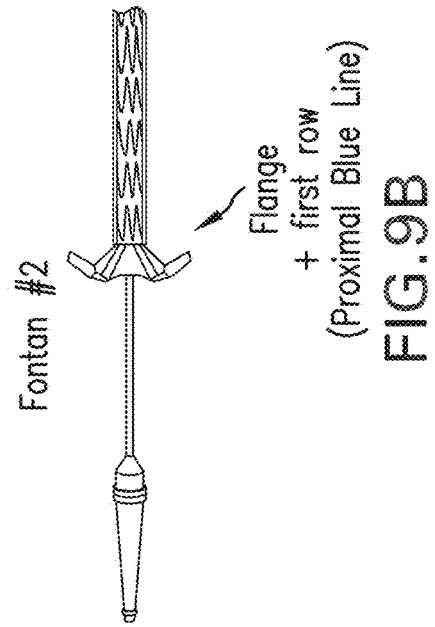
FIG. 9B
FIG. 9C

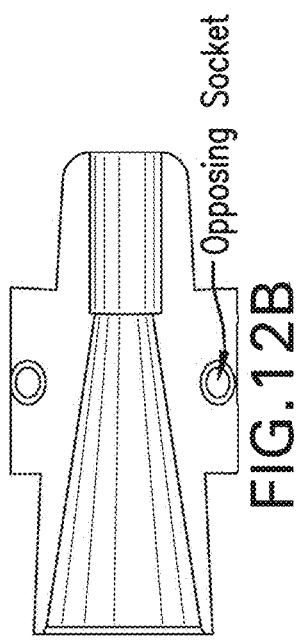
FIG. 12A
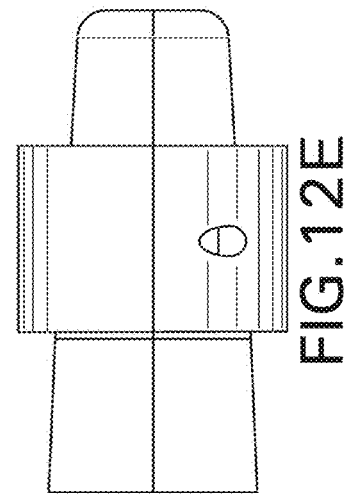
FIG. 12B
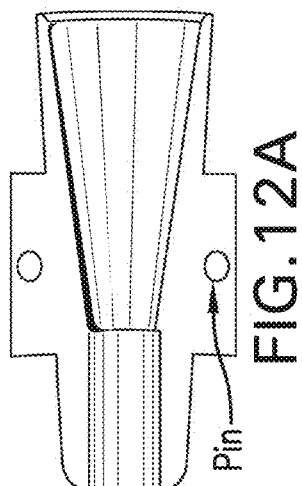
FIG. 12C
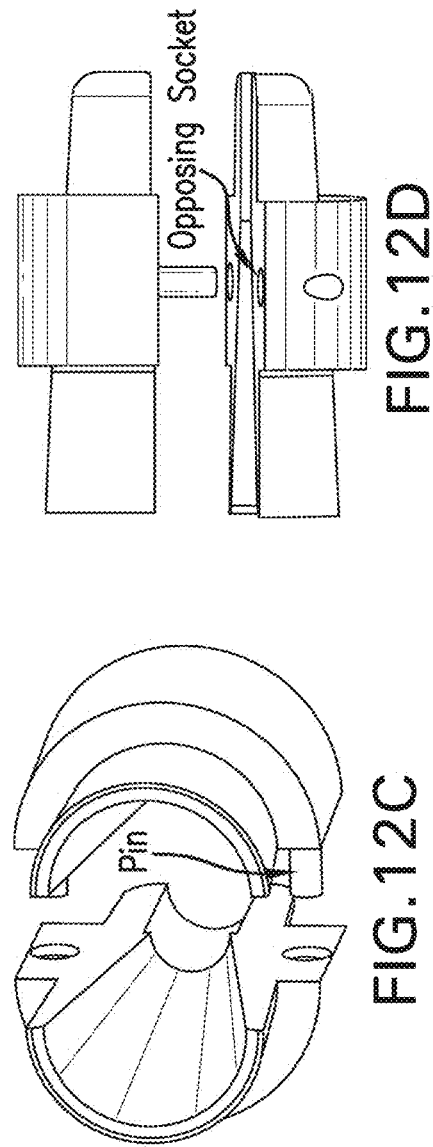
FIG. 12D
FIG. 12E Lumen of Delivery Shaft Aligned with Bottom of Taper Delivery Shaft Inserted up to Step

DEVICES AND METHODS FOR EFFECTUATING PERCUTANEOUS SHUNT PROCEDURES

CROSS-REFERENCE TO RELATED APPLICATIONS

The present patent application is a continuation of and claims the benefit of priority to U.S. patent application Ser. No. 16/399,670, filed Apr. 30, 2019, which is a continuation of and claims the benefit of priority to U.S. patent application Ser. No. 15/267,075, filed Sep. 15, 2016, now U.S. Pat. No. 10,426,482, which in turn claims the benefit of priority to U.S. Provisional Patent Application Ser. No. 62/219,118, filed Sep. 15, 2015, and U.S. Provisional Patent Application Ser. No. 62/363,716, filed Jul. 18, 2016. Each of the foregoing patent applications is incorporated by reference herein for any purpose whatsoever.

FIELD OF THE DISCLOSURE

The present disclosure relates to devices and methods for transcatheter (i.e., performed through the lumen of a catheter) Glenn shunt and Fontan systems (transcatheter cavopulmonary bypass endograft prosthesis and delivery) for nonsurgical, percutaneous extra-anatomic bypass between two adjacent vessels.

BACKGROUND

Children born with single ventricle physiology (SVP), a form of cyanotic congenital heart disease (CCHD), represent 7.7% of all congenital heart disease patients and have a birth incidence of approximately 4-8 per 10,000. In the United States, this represents approximately 2,000 children born each year. Currently, SVP infants undergo a series of staged surgical procedures. The first palliative procedure establishes a balance between systemic and pulmonary output while minimizing the overload on the single ventricle. The following palliative procedure is often cavopulmonary anastomosis through a bidirectional Glenn shunt or hemi-Fontan procedure to allow for passive pulmonary bloodflow. These are surgical procedures that are invasive and traumatic, requiring significant recuperation time and excessive burden on such a young patient.

SUMMARY OF THE DISCLOSURE

The purpose and advantages of the present disclosure will be set forth in and become apparent from the description that follows. Additional advantages of the disclosed embodiments will be realized and attained by the methods and systems particularly pointed out in the written description hereof, as well as from the appended drawings.

A transcatheter approach for obtaining the results of the surgical procedures described above can revolutionize the management of these children with congenital heart disease. As an alternative to the Norwood Procedure, Bi-directional Glenn operation and Fontan procedure, a nonsurgical transcatheter intervention can limit the burden of surgery for infants while also reducing cost. There is a considerable unmet need for a purpose-built cavopulmonary anastomosis device. To Applicant's knowledge no commercial alternatives exist for off-label medical use.

To achieve these and other advantages and in accordance with the purpose of the disclosure, as embodied herein, in one aspect, the disclosure includes embodiments of a cavopulmonary self-expanding implant to permit an interventional cardiologist to create a shunt between the Superior Vena Cava (SVC) and the main pulmonary artery (MPA). The implant can provide an urgently needed option for children with congenital heart failure to avoid the burden of a three-stage surgery (so called palliative surgery), the burden of an additional heart transplantation after failure of the palliative surgeries, or of the lifelong medication intake after direct heart transplantation.

In some implementations, a radially self-expanding endograft prosthesis is provided that includes (i) distal flange that is self-expanding and configured to flip generally perpendicularly with respect to a body of the prosthesis to help seat the prosthesis against a tissue wall, (ii) a distal segment extending proximally from the distal flange that has sufficient stiffness to maintain a puncture open that is formed through a vessel wall (iii) a compliant middle segment extending proximally from the distal segment, the middle segment being more compliant than the distal segment, and having independently movable undulating strut rings attached to a tubular fabric, the combined structure providing flexibility and compliance to allow for full patency while flexed, the segment being configured to accommodate up to a 90 degree bend, (iv) a proximal segment having a plurality of adjacent undulating strut rings that are connected to each other, the proximal segment being sufficiently stiff to seat within and urge against a vessel wall, and (v) a proximal end including a plurality of openings around the proximal end for accommodating a tether that is threaded through the openings to cause the prosthesis to collapse radially inwardly when tension is applied to the tether.

In some implementations, a delivery system is provided including the prosthesis as set forth above, wherein the prosthesis is mounted on a longitudinal inner member and inside of a retractable sheath. Both ends of the tether that is routed through the prosthesis can extend proximally through and out of a proximal region of the delivery system. The delivery system can further include a first set of radiopaque markers near the distal end of the delivery system, and a second set of markers that are visible outside the patient during a procedure that indicates the relative position of the delivery system and prosthesis, wherein the first and second set of markers are maintained in registration with each other during the procedure. The first set of markers can be located on a distal atraumatic tip of the delivery system made of iron oxide to facilitate navigation under MRI or other imaging modality to position the delivery system accurately, and the second set of markers can indicate the relative longitudinal position of the portions of the delivery system. The markers can be configured to indicate when the distal flange of the prosthesis is suitably configured to pull against an inner face of the wall of an artery, such as main pulmonary artery.

The prosthesis can further include a flared or bell-shaped proximal region to enhance apposition against the interior wall of a lumen. The prosthesis can further define at least one fenestration through a sidewall thereof to permit leakage of bodily fluid through the fenestration.

In some implementations, a tubular prosthesis is provided having a first flanged end and a second flanged end, each flanged end being configured to urge against an inner surface of a first body lumen and a second body lumen when the prosthesis is mounted through openings formed into the walls of the first body lumen and second body lumen. The prosthesis can be adjusted in length. The prosthesis can include proximal and distal portions connected by a central elastic region such that the prosthesis can be stretched to cause the flanged ends of the prosthesis to pull against the lumens that the flanged ends are mounted into.

It is to be understood that both the foregoing general description and the following detailed description are exemplary and are intended to provide further explanation of the embodiments disclosed herein.

The accompanying drawings, which are incorporated in and constitute part of this specification, are included to illustrate and provide a further understanding of the method and system of the disclosure. Together with the description, the drawings serve to explain the principles of the disclosed embodiments.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIG. 2A-FIG. 2C illustrate use of the loading tool of FIG. 12 to load a prosthesis such as that of FIG. 1A onto a delivery system.

FIG. 7 is an image of prostheses deployed in Glenn and Fontan procedures in a test animal in accordance with the disclosure.

FIG. 9A-FIG. 9E are illustrations of further aspects of the illustrative prostheses and delivery systems in accordance with the disclosure.

FIGS. 12A-12H are illustrations of a prosthesis loading tool in accordance with the disclosure.

DETAILED DESCRIPTION

Reference will now be made in detail to the present preferred embodiments of the disclosure, examples of which are illustrated in the accompanying drawings. The method and corresponding steps of the disclosed embodiments will be described in conjunction with the detailed description of the system. The exemplary embodiments illustrated herein can be used to perform Glenn and Fontan procedures, but percutaneously. It will be appreciated, however, that the disclosed embodiments, or variations thereof, can be used for a multitude of procedures involving the connection of blood vessels or other biological lumens to native or artificial structures.

Embodiments of a disclosed TCBE (Transcatheter Cavopulmonary Bypass Endograft) represent a potential breakthrough for physicians and young patients who require a safe, less-burdensome, and effective alternative to open heart surgery: a percutaneous approach to heal congenital heart failure.

In particular implementations, the underlying design of the TCBE is based on four components: (i) a distal segment, which is divided into a flange (consisting of a multi-pointed (e.g., six-pointed) star) and two to four rows of connected (e.g., by stitching) undulating wire segments; (ii) a middle segment, which includes longer non-connected undulating wire segments, (iii) and the largest, proximal, segment, which is useful for bridging and stabilization of the implant in the vessel. Depending on the size of the implant, it can be built as a "Glenn Shunt" (about 5 cm in length) or a "Fontan Shunt" (about 8 cm in length). These can be, for example, super elastic Nitinol-supported tubular polyester fabric implants that are delivered through a specially designed delivery system. Preferably, the prosthesis and delivery system are both MRI compatible. The illustrated TCBE embodiments can incorporate several useful features specifically developed for transcatheter cavopulmonary bypass.

Figure 1A:
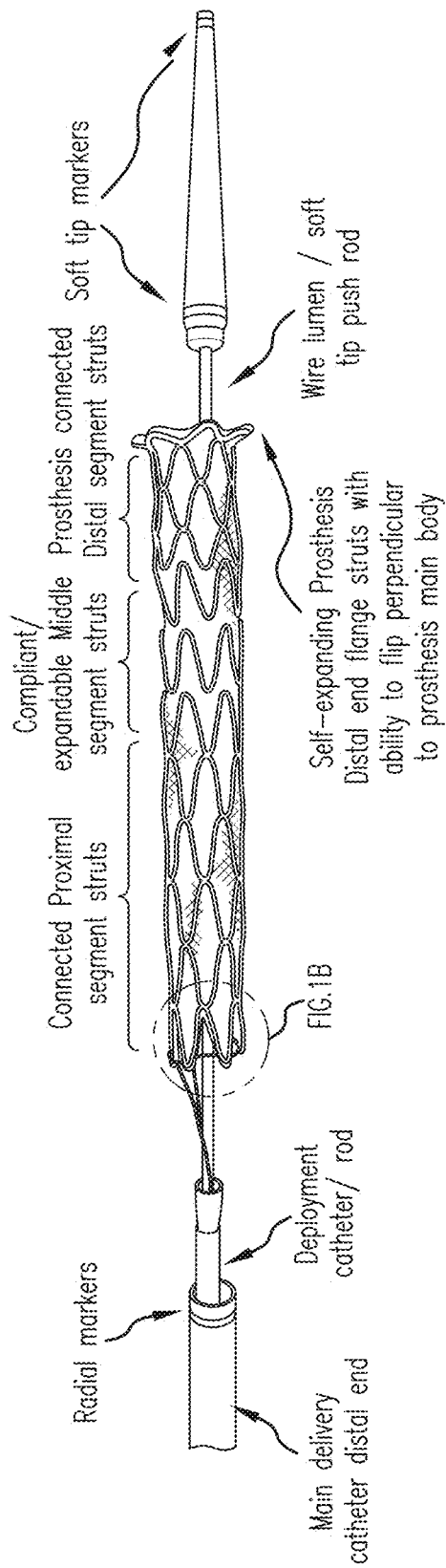
FIG. 1A depicts a view of a self-expanding prosthesis for performing a Glenn procedure disposed about a distal region of a delivery system for the prosthesis.
Figure 1B:
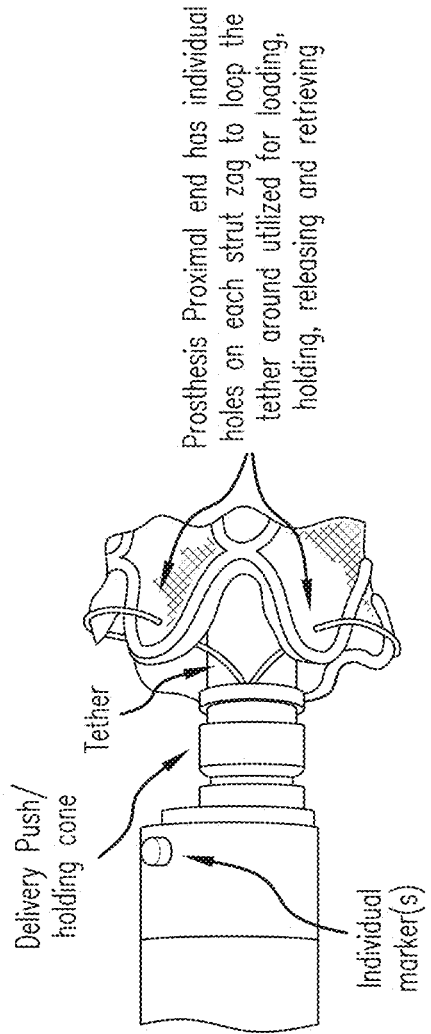
FIG. 1B depicts a close-up view of a portion of the prosthesis depicted in FIG. 1A.

For purposes of illustration, and not limitation, as embodied herein and as illustrated in FIG. 1, a prosthesis is provided for transcatheter cavopulmonary bypass situated on a distal region of a delivery system. As can be seen, the device has a tubular stent-like structure formed from ring shaped segments that have an undulating "zig-zag" pattern. A first, proximal end of the prosthesis has an undulating end defined by the proximal-most ring of the prosthesis. The distal end has a similar undulating end formed from a ring of undulating material, but the material is heat treated such that it "flips" from a first direction that is generally parallel to a central longitudinal axis of the prosthesis, and relaxes into a bent over flange having a tip that is generally perpendicular to the longitudinal axis of the prosthesis when permitted to expand. The flange can be oriented at any suitable angle with respect to the longitudinal axis, and is preferably perpendicular thereto, or forms a slightly acute angle with respect to the wall of the prosthesis (e.g., between 70 and 90 degrees). The flange is useful for pulling against the inside of a vessel or other tissue wall when the remaining prosthesis is advanced through an opening in such vessel or other tissue wall, preventing pull through, and permitting a facilitated anastomosis procedure generally, as well as for Glenn and Fontan procedures.

As can be seen, the proximal end of the prosthesis receives a tether therethrough that is routed through the windings of the undulating ring. The tethers are withdrawn proximally through a tubular member (e.g., a sheath) that also passes a core member therethrough that forms the core, or push rod of the delivery system. The core is slidably disposable with respect to the sheath. By advancing the core member with the prosthesis mounted thereto distally outwardly of the sheath, the prosthesis self-expands. However, if the tether is tensioned, it causes the proximal end of the prosthesis to collapse radially inwardly such that the prosthesis can be withdrawn into the sheath. While adjacent undulating rings of the prosthesis particularly near the distal end of the prosthesis can be connected to each other (e.g., by sewing), they can also be kept independent of one another, and be attached to an inner and/or outer tubular fabric layer. The rigidity of the prosthesis is selected and/or configured to provide a desired performance. Thus, the distal end is relatively rigid to maintain an opening in the wall of a vessel or other organ in an open state that the prosthesis traverses through by resisting the force of the vessel wall to want to "close" the hole in itself. The proximal region is less rigid and can accommodate increasing vessel curvature of the vessel that it is mounted in.

The delivery system typically includes an atraumatic distal tip that can pass a guidewire therethrough, and may be provided with one or more radiopaque markers to facilitate visualization under fluoroscopy, for example. The distal end or end region of the sheath of the delivery system (that surrounds the prosthesis when loaded onto the delivery system) can also include a radiopaque marker.

Figure 3A:
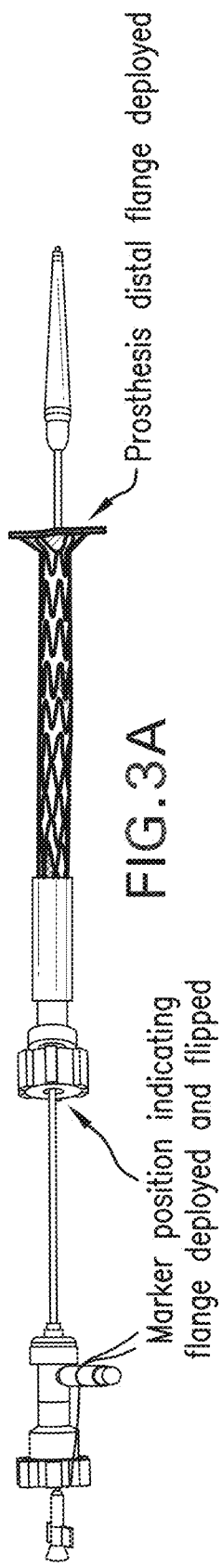
FIGS. 3A-FIG. 3B illustrate a prosthesis delivery system in its initial deployment position.
Figure 3B:
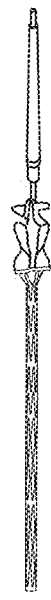
Figure 3C:
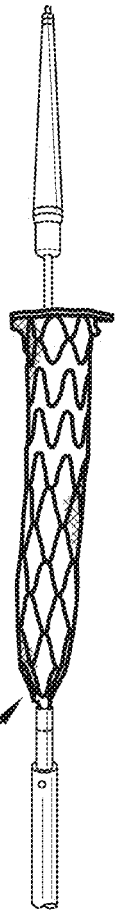
FIG. 3C illustrates the prosthesis fully deployed but threaded with a retraction tether.
Figure 3D:
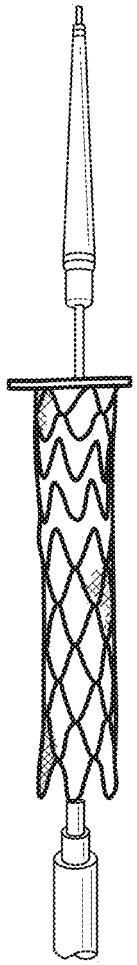
FIG. 3D illustrates the prosthesis fully deployed with the retraction tether removed.

FIGS. 2A-2D illustrate loading of the prosthesis on the core member of the delivery system using a clam shell like loading tool described in further detail below with respect to FIG. 12. FIG. 2C illustrates the delivery system in a collapsed condition. The delivery system includes the aforementioned core member defining a guide wire lumen therethrough. The sheath is fitted over the core, and the tethers run between the components in the annular space between the core and sheath. As shown in FIG. 3A, the flared distal end of the prosthesis flips over from zero to 90 degrees as the sheath is advanced proximally. The proximal end of the prosthesis is held radially inwardly by the tether until tension of the tether is released. Tension can be reapplied to the tether to permit the prosthesis to be fully removable unless the tether is removed.

Figure 4E:
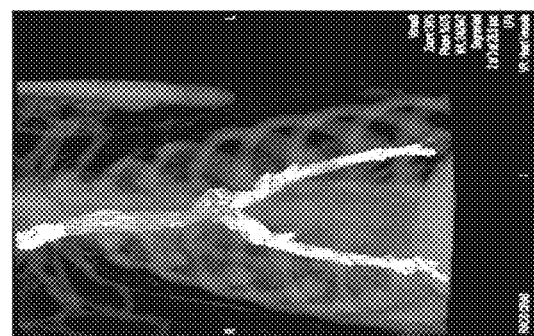
FIG. 4E shows a scan of a fully deployed percutaneous cavopulmonary bypass endograft self-expanding prosthesis in a large porcine model used in a Glenn procedure.
Figure 4D:
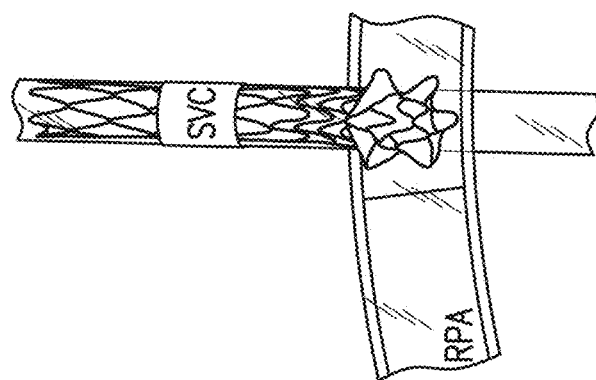
FIG. 4D shows a model of a Glenn shunt prosthesis in accordance with the disclosure being deployed in the main pulmonary artery (MPA) and the superior vena cava (SVC).
Figure 4C:
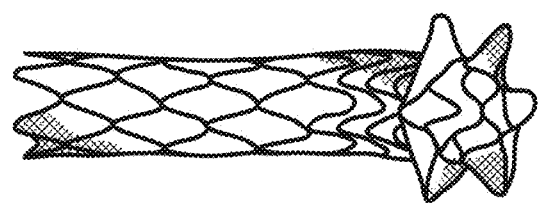
FIG. 4C illustrates the articulated prosthesis of FIG. 4B to show the flared distal end.
Figure 4B:
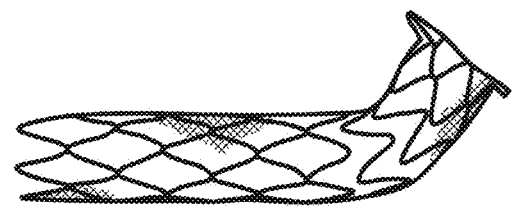
FIG. 4B illustrates the same prosthesis being articulated to the right at its distal end.
Figure 4A:
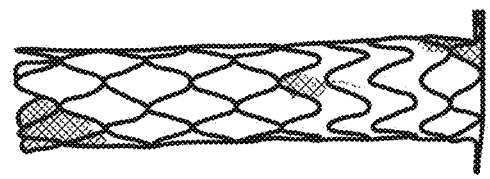
FIG. 4A illustrates an exemplary prosthesis for a Glenn procedure, for example, in a deployed condition.

FIG. 4a shows the disclosed prosthesis for a Glenn procedure. The distal region on the prosthesis is flexible to permit passage of the prosthesis through a curved vessel. FIG. 4D shows the distal flanged end of the prosthesis pulling against the inner wall of the main pulmonary artery (MPA), with the proximal end of the prosthesis extending into the superior vena cava in a Glenn procedure.

Figure 5A:
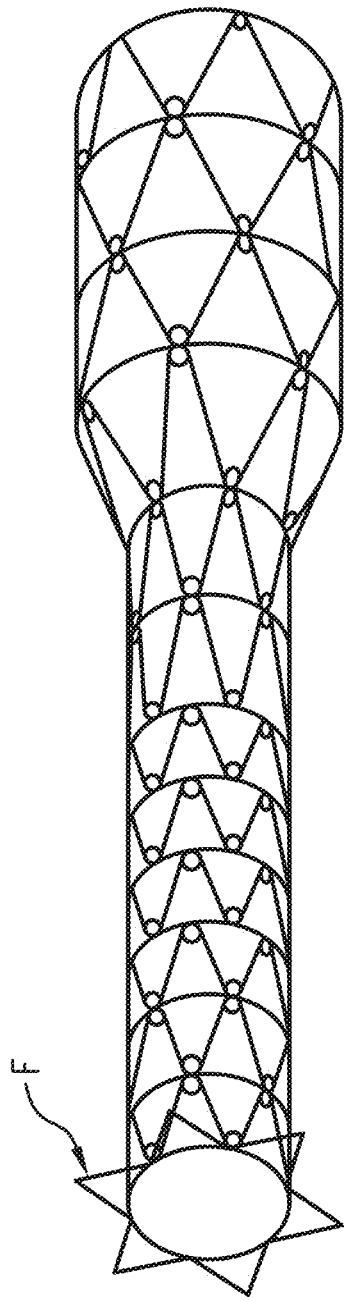
FIG. 5A is an isometric schematic view of an illustrative prosthesis for use in a Fontan procedure.
Figure 5B:
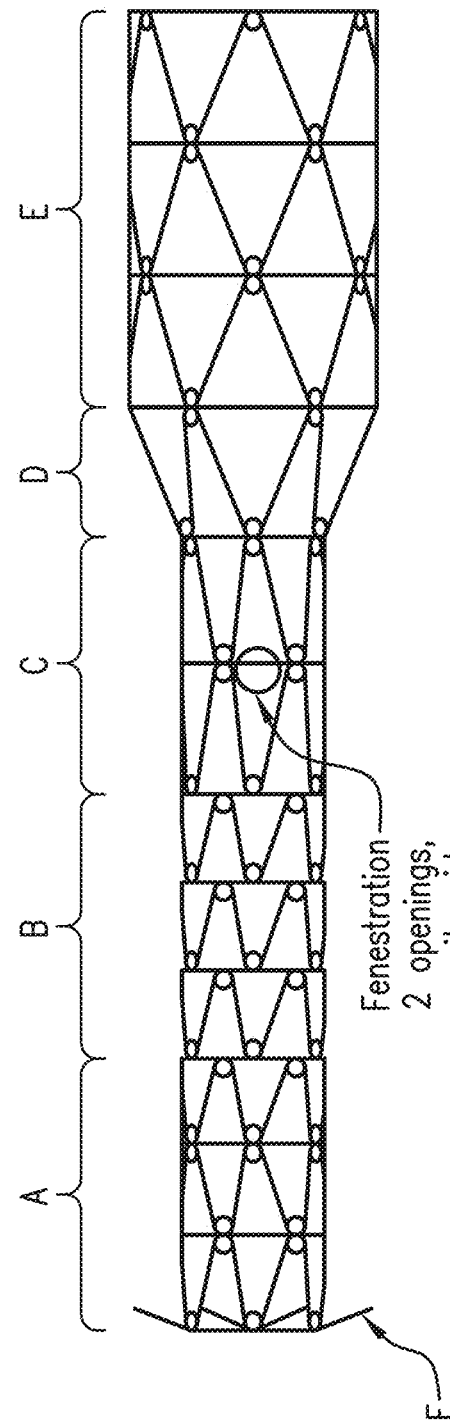
FIG. 5B is a plan view of such a prosthesis.

FIG. 5A shows a schematic perspective view of a Fontan-type prosthesis, and FIG. 5B shows a side view schematic of such a prosthesis. Adjoining rings of the framework of the prosthesis are attached (e.g., by stitching) to a tubular fabric that preferably passes through the rings of the framework, wherein the framework is made, for example, of 0.014 inch diameter NiTi. The longitudinal dimension of each structural ring can be different. For example, region "A" of the prosthesis can be comparatively stiff, wherein the rings can be attached to each other directly or via the fabric, wherein regions B, C, D, and E can have different, lower stiffnesses.

Figure 6B:
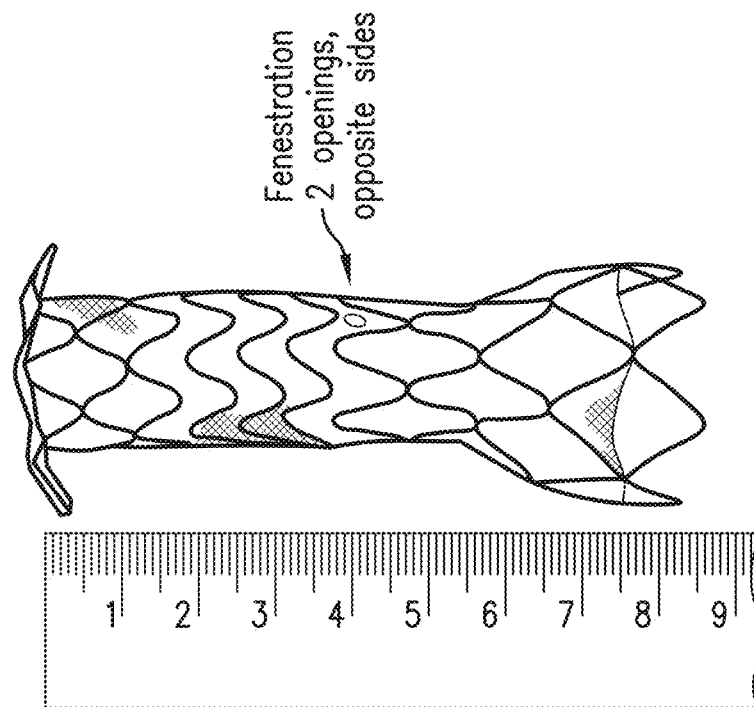
FIG. 6B is a second illustrative embodiment of a prosthesis for use in a Fontan procedure.
Figure 6A:
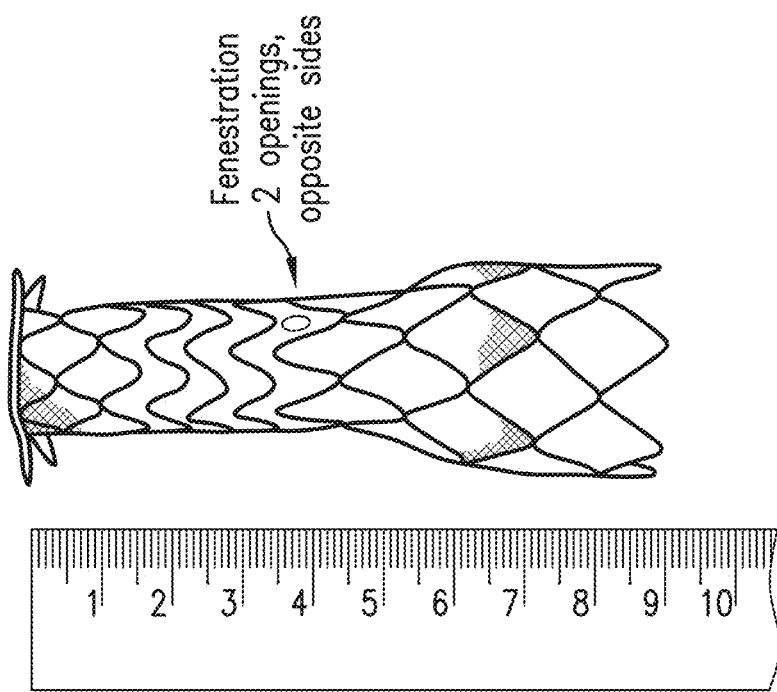
FIG. 6A is a first illustrative embodiment of a prosthesis for use in a Fontan procedure.

FIG. 6A illustrates a first embodiment of a prosthesis for a Fontan procedure. The body is similar to that of the prosthesis in FIG. 5, but is made, for example, from 0.013 inch diameter Ni Ti wire. FIG. 6B illustrates a second embodiment that is also formed from the same wire, but the flange is formed at a steeper angle to create an increased flip, or displacement, of the distal flange when the prosthesis is deployed. The prosthesis can include one or more (e.g., 2) fenestrations through the fabric in a central region thereof to permit leakage into the right atrium when the prosthesis spans from its distal end situated within the main pulmonary artery to the superior vena cava.

The star shaped flange on the end of each prosthesis helps the prosthesis seat well within the vasculature. In some embodiments the tethers can be routed through parallel lumens along the length of the delivery system to prevent them from tangling with each other. The prosthesis for the Fontan procedure preferably includes a proximal region that flares out, as illustrated in FIG. 6B to provide enhanced wall apposition.

FIG. 7 illustrates an animal model wherein two prostheses are installed as disclosed herein using the disclosed delivery system; one in a Glenn procedure (connecting the SVC to the MPA to supply blood from the superior vena cava (SVC) to the main pulmonary artery (MPA)), and one in a Fontan procedure (connecting the inferior vena cava (IVC) through the ventricle to the main pulmonary artery (MPA)), wherein the prosthesis includes fenestrations to permit leakage through the prosthesis into the ventricle.

Figure 8E:
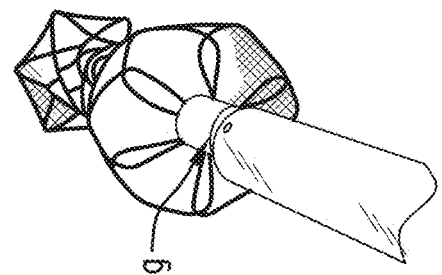
FIG. 8A-FIG. 8E are illustrations of various aspects of a method of deploying a prosthesis in accordance with the disclosure.
Figure 8D:
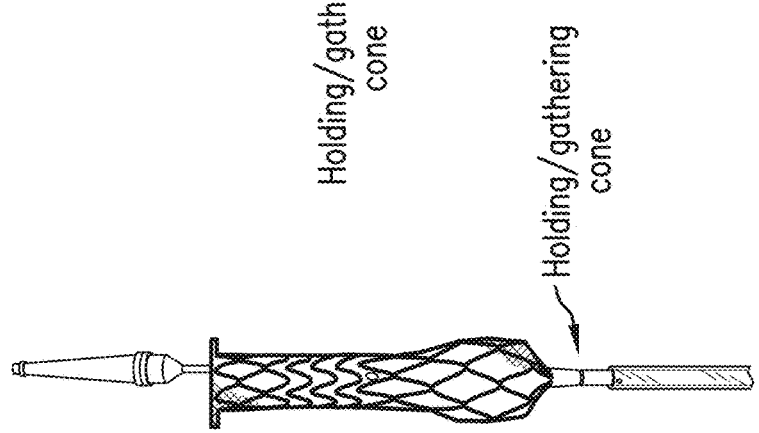
Figure 8C:
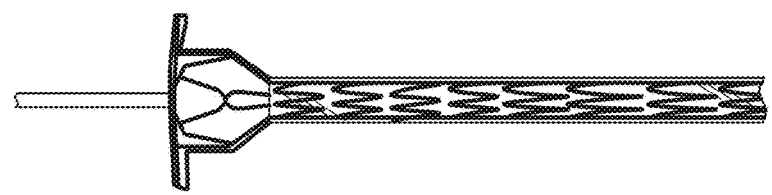
Figure 8B:
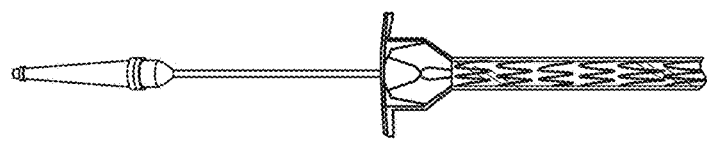
Figure 8A:

FIG. 8A shows the delivery system with the prosthesis (for the Glenn or Fontan procedure) mounted thereon. FIG. 8B shows the core and distal tip advanced distally, and the distal flared end of the prosthesis deployed. FIG. 8C shows a close up of the flared distal end of the prosthesis. FIG. 8D shows the prosthesis mostly deployed, but the tether tensioned so as to keep the proximal end of the prosthesis held radially inwardly. FIGS. 9A and 9B show two different embodiments of a prosthesis as described above, FIG. 9C shows the prosthesis collapsed and within a sheath of the delivery system, whereas FIG. 9D shows the proximal ends of the delivery systems for each prosthesis. FIG. 9E shows differing sizes of distal tips that can be used, depending on the application. The distal tip acts as a strain relief from a guidewire extending distally outwardly of a central guidewire lumen of the device. As such, while it is preferable to have the tip be relatively long, it is also useful to have it not be too long so as to prevent the delivery system from navigating a relatively narrow lumen when entering it obliquely.

Figure 10A:
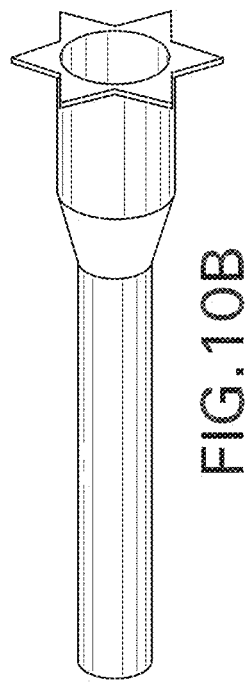
FIG. 10A, B-FIG. 10C, D are illustrations of two further embodiments of prostheses in accordance with the disclosure.
Figure 10B:
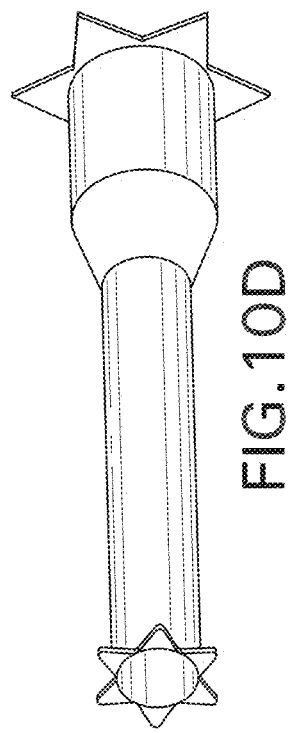
Figure 10C:
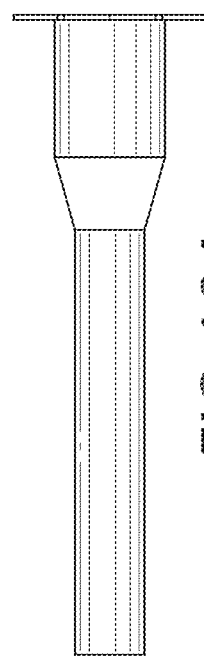
Figure 10D:
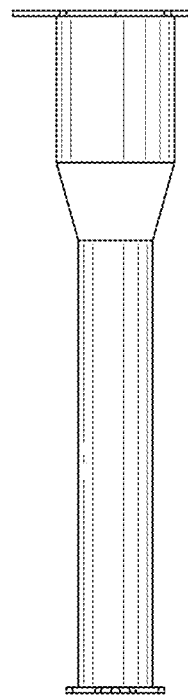

FIGS. 10A-10B show side and isometric views of a prosthesis having a flanged distal end. FIGS. 10CA-10D show side and isometric views of a prosthesis having a flanged distal end as well as a flanged proximal end (upon prosthesis deployment). The illustrated prostheses also include a first section of relatively large diameter, such as near the flanged end, that transitions to a region of lower diameter by way of a transition region. The prosthesis can also be of adjustable telescoping length. The inside diameter preferably remains substantially unchanged when the prosthesis is adjusted in length.

Figure 11A:
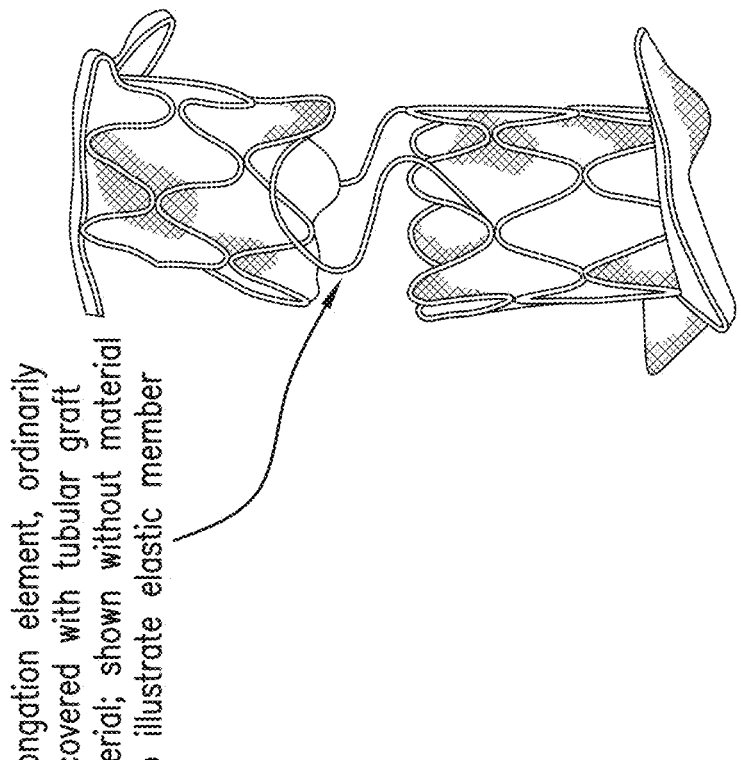
FIGS. 11A-11B are illustrations of a further embodiment of a prosthesis in accordance with the disclosure.
Figure 11B:
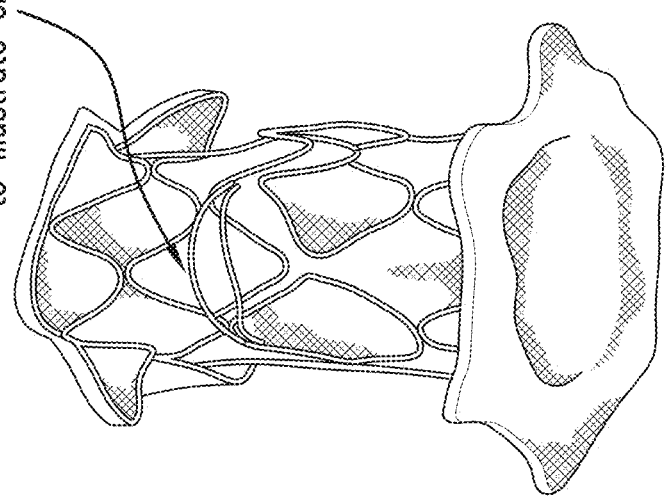

FIGS. 11A-11B show a flanged prosthesis of adjustable length having two flanged ends attached to tubular structural regions that are in turn structurally joined in a central region by an elastic member, such as a spring. A tubular fabric member preferably traverses the inside or the outside of the length of the prosthesis. The prosthesis is shown without such a tubular fabric member for illustrative purposes, and each end can be of a different diameter from the other. Such a prosthesis can be useful, for example, for forming a shunt from the descending aorta to the main pulmonary artery to decompress the aorta. The length can be adjusted of the prosthesis, and tension can be maintained on the prosthesis by way of the spring, helping the flanged ends to seat against the inner walls of the aorta and the MPA.

Figure 12G:
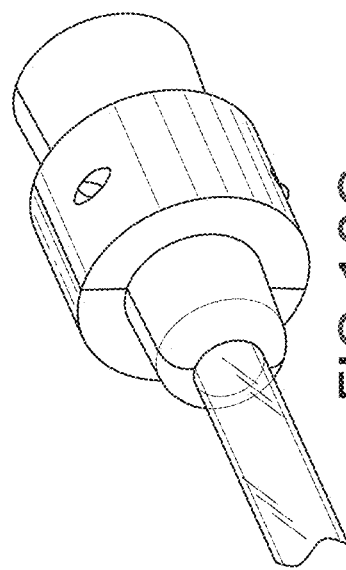
Figure 12H:
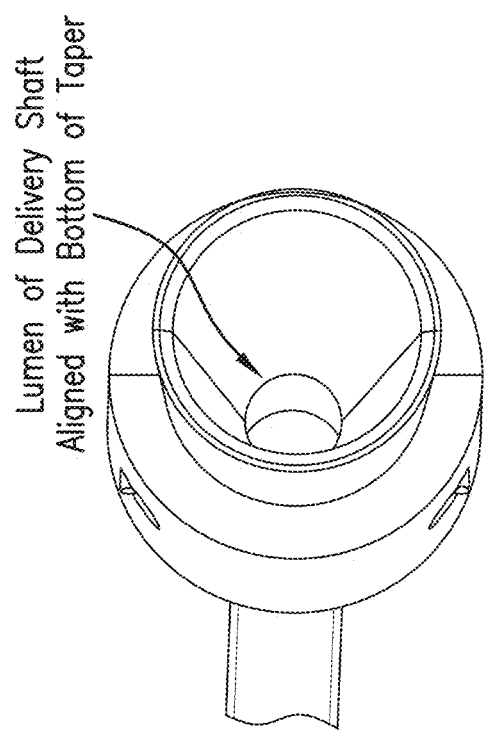
Figure 12F:
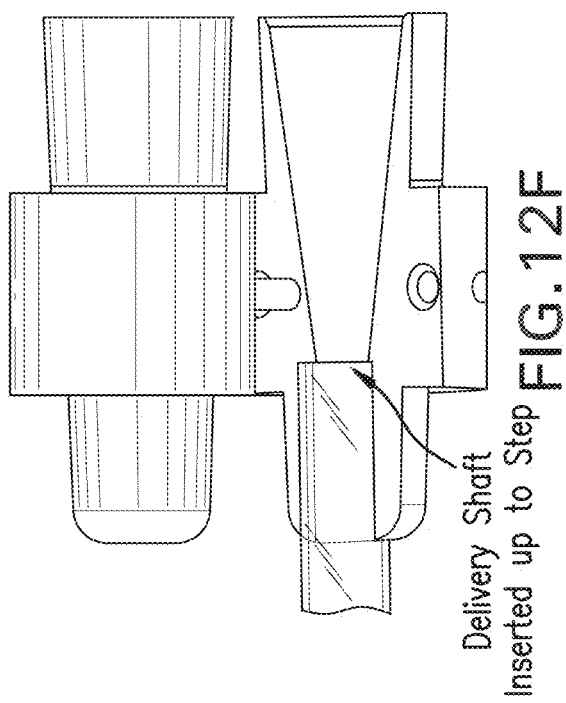

FIGS. 12A-12H illustrate aspects of a prosthesis loading tool in accordance with the disclosure. As illustrated, the loading tool includes two halves, the inner faces of which are illustrated in FIGS. 12A and 12B. An interior channel including a first funnel portion necking down from a relatively large diameter to a relatively small diameter transitions into a second region of constant diameter, but wherein a step, or shoulder is present on the region of smaller diameter that effectively results in the funnel portion having a slightly smaller diameter than the region of constant diameter. As illustrated in FIGS. 12C-12E, the two halves align and mate with each other by way of a pair of protrusions on one half of the tool being received by a pair of indentations, or holes, on the other half of the tool. In use, the distal end of the sheath that will cover the prosthesis is inserted into the end of the prosthesis having the portion of constant diameter until it abuts the shoulder. In use, the central shaft of the delivery system passes through the sheath and the funnel section. The prosthesis, loaded with the tether on its proximal end, is then advanced into the funnel and is necked down to fit inside the sheath, but surrounding the central shaft, or tubular core member, of the delivery system. Advancing the prosthesis into the funnel section helps effectuate the compression. After the prosthesis is loaded, the loading tool is simply removed.

Generally, during deployment, the delivery system is advanced to a position where the prosthesis should be deployed. The distal tip and core of the guidewire are then advanced distally as well as the prosthesis, and the prosthesis flange is deployed thorough an opening in a wall of a vessel or other tissue wall. The flanged end then urges against the inner wall of the vessel. A corresponding marker can be used on the proximal end of the delivery system to show at what point of relative advancement the flange has been deployed. The delivery system is then pulled proximally slightly to seat the flange. When satisfied with seating, the user holds the inner shaft of the delivery system and pulls back on outer sheath to release the entire implant. The tether can then be de-tensioned to open the proximal end of implant. Finally, the user can pull on one end of the tether to remove it from the implant, and the delivery system can be removed. However, if desired, prior to removal of the tether, the tether can be re-tensioned, causing the proximal end of the prosthesis to collapse radially inwardly, and the prosthesis can be withdrawn into the sheath of the delivery system, and removed.

The devices and methods disclosed herein can be used for other procedures in an as-is condition, or can be modified as needed to suit the particular procedure. In view of the many possible embodiments to which the principles of this disclosure may be applied, it should be recognized that the illustrated embodiments are only preferred examples of the disclosure and should not be taken as limiting the scope of the disclosure.

What is claimed is:

1. A method of installing a tubular prosthesis through a sidewall of a native lumenal vessel, comprising:
    providing a prosthesis having:
        a distal annular flange configured to help seat the prosthesis when it is pulled proximally;
        a distal tubular segment extending proximally from the distal flange that has sufficient stiffness to maintain a puncture in an open condition that is formed through a first vessel wall through which the distal segment passes; and
        a proximal tubular segment that is sufficiently stiff to seat within and urge against a second vessel wall;
    wherein the prosthesis includes at least one marker that is visible from outside the patient using an imaging modality, wherein the at least one marker of the prosthesis includes radiopaque material or iron oxide;
    collapsing the prosthesis onto a delivery system, wherein the delivery system includes at least one marker that is visible from outside the patient using the imaging modality, wherein the at least one marker of the delivery system includes radiopaque material or iron oxide;
    delivering a distal end of the delivery system to an opening defined through a native lumenal vessel wall;
    deploying the distal annular flange inside of the native lumenal vessel wall; and
    maintaining the at least one marker of the prosthesis and the at least one marker of the delivery system in registration with each other during at least a portion of the method.

2. The method of claim 1, further comprising pulling proximally on the delivery system to seat the distal annular flange.

3. The method of claim 2, further comprising deploying the distal tubular segment from the delivery system.

4. The method of claim 3, further comprising deploying the proximal tubular segment from the delivery system.

5. The method of claim 4, wherein the proximal tubular segment is deployed inside of a second lumenal vessel.

6. The method of claim 5, wherein the prosthesis further includes a proximal annular flange coupled to the proximal tubular segment, and further wherein the method further comprises deploying the proximal annular flange inside of the second lumenal vessel against an inner wall of the second lumenal vessel.

7. The method of claim 5, wherein the proximal tubular segment is deployed in a second lumenal vessel and further wherein the proximal tubular segment is urged against an inner wall of the second lumenal vessel.

8. The method of claim 4, further comprising de-tensioning a tether directed through a proximal end of the implant to open the proximal end of the implant.

9. The method of claim 8, further comprising pulling on one end of the tether to remove the tether from the implant.

10. The method of claim 8, further comprising re-tensioning the tether to cause the proximal end of the prosthesis to collapse radially inwardly.

11. The method of claim 10, further comprising withdrawing the prosthesis into a sheath of the delivery system.

12. The method of claim 8, wherein both ends of the tether are directed proximally through and out of a proximal region of the delivery system, and further wherein tension is applied from outside a patient being treated.

13. The method of claim 1, wherein the at least one marker of the prosthesis and the at least one marker of the delivery system are visible under MRI, and further wherein the procedure is conducted while imaging using a MRI imaging modality in real time.

14. The method of claim 1, wherein the prosthesis includes distal markers proximate the distal flange, and further wherein the method includes observing when the distal markers are aligned with the opening in the native lumenal vessel wall.

15. The method of claim 1, wherein the prosthesis further includes a flared or bell-shaped proximal region, and further wherein the method includes deploying the flared or bell shaped proximal region against the interior wall of a lumen.

16. The method of claim 1, wherein the prosthesis further defines at least one fenestration through a sidewall thereof and further wherein the method includes positioning the prosthesis in a manner that permits leakage of bodily fluid through the fenestration.

17. The method of claim 1, wherein the prosthesis can be adjusted in length, and further wherein the method includes adjusting the prosthesis in length when installing the prosthesis.

18. The method of claim 1, wherein the at least one marker of the prosthesis and the at least one marker of the delivery system are visible under fluoroscopy, and further wherein the procedure is conducted while imaging using a fluoroscopic imaging modality in real time.

\* \* \* \* \*